United States Patent [19]
Labriola, II

[11] Patent Number: 5,428,470
[45] Date of Patent: Jun. 27, 1995

[54] MODULAR SYSTEM AND METHOD FOR AN AUTOMATIC ANALYZER

[75] Inventor: Donald P. Labriola, II, La Verne, Calif.

[73] Assignee: Beckman Instruments, Inc., Fullerton, Calif.

[21] Appl. No.: 916,306

[22] Filed: Jul. 17, 1992

[51] Int. Cl.⁶ .......................................... G01N 33/00
[52] U.S. Cl. ................................. 359/119; 364/497; 364/496; 422/62; 422/67; 436/50; 436/55
[58] Field of Search ............................. 359/119, 173; 340/870.02, 650, 870.39, 870.19, 825.06, 318, 685; 385/15; 307/149, 150, 154; 422/62, 67; 356/246; 436/50, 55; 364/497, 496

[56] References Cited

U.S. PATENT DOCUMENTS

| | | | |
|---|---|---|---|
| 4,052,161 | 10/1977 | Atwood et al. | 23/230 |
| 4,446,412 | 5/1984 | Friedman et al. | 318/696 |
| 4,467,961 | 8/1984 | Coffee et al. | 239/1 |
| 4,540,928 | 9/1985 | Marhoefer | 318/696 |
| 4,583,033 | 4/1986 | Uehara et al. | 318/696 |
| 4,591,774 | 5/1986 | Ferris et al. | 318/696 |
| 4,621,200 | 11/1986 | Lovrenich | 307/149 |
| 4,631,657 | 12/1986 | Hill et al. | 318/696 |
| 4,705,960 | 11/1987 | Lovrenich | 307/149 |
| 4,734,847 | 3/1988 | Hunter | 318/696 |
| 4,761,598 | 8/1988 | Lovrenich | 318/696 |
| 5,179,376 | 1/1993 | Pomatto | 340/870.02 |

OTHER PUBLICATIONS

"Smart Motor Integrates Hardware and Software", by Sam Davis, *PCIM*, Apr., 1989, pp. 6-8.

"High Performance Brushless DC Motors for Direct Drive Robot Arm," by Steve Davis, and Dan Chen, *PCIM*, Aug., 1985, pp. 34-38.

"Intelligent Position Control Employs Motor with Internal Feedback," by William Seitz, *PCIM*, Jun., 1986, pp. 47-54.

"Principles of Vector Control—Part II," by Dr. Dal Ohm, *PCIM*, Sep., 1990, pp. 32-36.

"Permanent-Magnet Steppers Edge into Servo Territory," by R. Horber, *Machine Design*, Nov. 12, 1987, pp. 99-102.

"Motion Controller Employs DSP Technology," by R. van der Kruk and J. Scannell, *PCIM*, Sep., 1988, pp. 94-101.

"An Alternative to Choosing Between DC And Stepper Motors," by Dr. C. Oudel and D. Ettelman, *Powerconversion International*, May, 1985, pp. 50-58.

"General Purpose Motion Control IC," published by Hewlett Packard, Technical Data Nov., 1985.

Primary Examiner—Hezron E. Williams
Assistant Examiner—Richard A. Moller
Attorney, Agent, or Firm—William H. May; Arnold Grant; Merchant & Gould

[57] ABSTRACT

An automated analytical system module design essentially electrically isolates modular elements within the analyzer system with inter-module communications provided via packet-based communications. The modules may include a motor controller which estimates motor temperature to enable high initial torque with motor failure prediction and detection. The modules in such a system can be identified on serial communications loops by a module reset and count-off process.

11 Claims, 10 Drawing Sheets

MODULAR SYSTEM AND METHOD FOR AN AUTOMATIC ANALYZER

FIELD

The present invention relates generally to the field of distributed control systems and more particularly to a control system and modules for use in automated systems, and still more particularly to such systems and modules for use in automated analyzers.

BACKGROUND

With the development of microprocessors, numerous processes and systems have been automated over the last three decades. As an example, automated clinical chemistry analyzers have developed to a point of substantial sophistication, with many such analyzers essentially being integrated collections of robots and other automatically controlled processes. The result is often a complex system including motion, fluid and temperature control along with photometers, ion selective electrodes and other sensing devices, all highly integrated and interdependent. An example of such a system is the SYNCHRON CX®7 automated clinical chemistry system available from Beckman Instruments, Brea, Calif., U.S.A.

However, as the complexity and integration of such systems has increased, the corresponding interdependence of the various subsystems can create problems with system integration, contributing to lengthened development time, complicated system modification, and increased difficulty in field service and maintenance. One aspect of such interdependence is often the common power supply that is provided throughout the system. Despite efforts to regulate such a power source for system-wide usage, and despite efforts the reduce or eliminate voltage drops and ground loops, the operation of one subsystem can often affect the operation of another subsystem through a common power bus. For example, a damaged "catch" diode across the coil of a solenoid can appear to be a variety of unrelated problems until the damaged diode is found.

Yet another aspect of such interdependence is the intra-system communication. Because of the complexity of these systems, a number of processors are used, some handling system-level tasks, such as system timing, and others handling the operation of specific functions, such as fluid probe movement and/or pump operation. Such intra-system communication has been achieved through the use of a common computer bus, including data, address and clock signals. Buses of this type quite typically are subject to noise and mechanical difficulties and, because such buses are transmission lines, changing loads can have an impact on digital wave form shapes transmitted along the buses. Further, by using these types of buses, conflict in the addresses of the various processors along the bus may be possible, further complicating the system design and integration.

Another difficulty in many prior art automated systems such as clinical chemistry analyzers is the use of a variety of motors in motion control, requiring corresponding development efforts for each motor. Further, despite the frequently large number of motion control motors used in advanced automated clinical chemistry analyzers, the fact that a motor that is experiencing a loss of performance, frictional binding or atypical loads is generally not known until the motor itself fails, causing down time for the analyzer and resulting in repair and service expense. Also, a motor that is operating near or at its functional limits may lead to intermittent failures that may be very difficult to detect during servicing.

Thus, there is a need for a system design that is easier to implement and where various automated devices that may be part of this system are less interdependent. There is also a need for a system that overcomes the prior-art difficulties encountered in intra-system communication. Also, there is a need for a system that tends to standardize the motion elements and which can detect motion element problems before the motion element, such as a stepper motor, fails.

SUMMARY

The present invention overcomes the limitations described with respect to prior art. According to the present invention, an automated system such as an automated clinical chemistry analyzer is divided into modularized processes based on individual modules, each module including the mechanical, electrical and computer control hardware and programming required for the operation of the module. Interconnection and interrelation with other modules within the system is minimized, to thereby decrease the likelihood that one automated assembly may interfere with the operation of another automated assembly, as is the case with the prior art.

Further, individual motion modules are standardized and power is monitored to optimize burst torque and to detect motor load overload problems before motor failure occurs.

The system may include plurality of functionally distinct modules, each such module including serial communications means for receiving and transmitting serial communications and power supply means for receiving power and producing power for use in the module. A bulk power supply means is provided for supplying bulk power to the power supply means in each module and a serial a serial communications loop that connects the serial communications means in the modules.

A module for use in a modular system in accordance with the present invention includes a first submodule portion including processing means for communication and control processing and optical serial communications means for receiving and transmitting optical serial communications. A second submodule portion includes power supply means for converting power and producing power for use in the module and function specific means for performing a specific function related to the module.

A method for identifying one or modules in an automated system in accordance with the present invention may be used where one or modules are included in a serial communications loop. The method may include the steps of transmitting a message from a master module, the message including a module identification number, receiving the message by a first module after the master module in the serial communications loop, verifying that a module identification number stored in the first module indicates that the first module is not the master module, storing the module identification number, transmitting a message with a module identification number incremented by a predetermined amount, and repeating the receiving step for additional modules in the serial communications loop.

Further a motor controller for controlling the position and a stepper motor according to the present invention includes encoder means for determining the rotational position of the motor shaft, means for receiving a motor shaft target position, and means for determining the difference between the target position and the present position of the motor shaft. Means is provided for determining a motor current according to the difference between the present position and the target position, calculating the estimated motor heating according to the current applied to the motor, and means for controlling the current applied to the motor according the required motor torque while limiting estimated motor heating.

FIGURES

DETAILED DESCRIPTION

Figure 1:
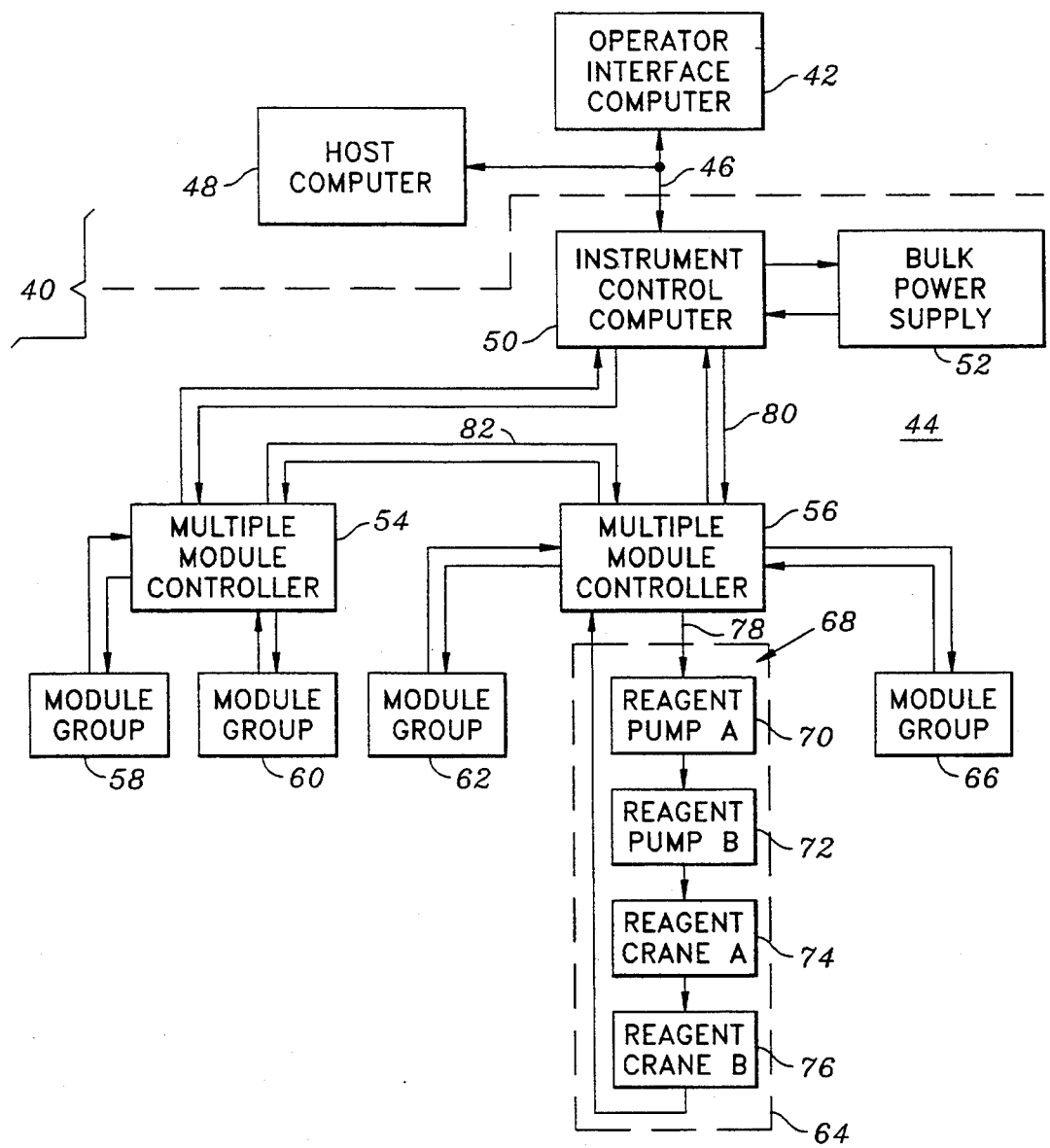
FIG. 1 is a block diagram of an automated analyzer in which the modular system and method of the present invention may be utilized.

With reference to FIG. 1, an automated system 40 that may utilize the modular system and method of the present invention is illustrated in functional block diagram form. The automated system 40 includes an operator interface computer 42 and an automated analyzer 44. The operator interface computer 42 communicates via a link 46 with the automated analyzer 44 and may also communicate via the link 46 with a laboratory or hospital host computer 48. The link 46 may be, for example, a high speed serial link such as an ethernet type network system and protocol as is well known in the art.

The link 46 is in communication with an instrument control computer 50 within the automated analyzer 44. The instrument control computer 50 is in turn in communication with an analyzer bulk power supply 52. The bulk power supply 52 provides a main, central power source for the automated analyzer 44 and is utilized by the modular system and method of the present invention as is described herein. The instrument control computer 50 is also in communication with a plurality of multiple module controllers and, in the embodiment illustrated in FIG. 1, it is particularly in communication with two multiple module controllers 54 and 56. Each multiple module controller 54, 56, is in turn in communication with respective module groups. More particularly, in the embodiment illustrated in FIG. 1, the multiple module controller 54 is in communication with module groups 58, 60 and the multiple module controller 56 is respectively in communication with module groups 62, 64 and 66.

The functional attributes of the automated system 40 of FIG. 1, such as sample and reagent handling, fluid control, analytical techniques and the like is of conventional design and may be similar, for example, to the Synchron CX 7 clinical system identified above. Such a system includes a central sample wheel for receiving samples, a batch processing unit for processing in parallel or in batch form a plurality of analytes, and a serial processing unit adapted to perform serial analysis of samples. Such systems and analytical techniques are well known in the art and are illustrated, for example, in U.S. Pat. Nos. 4,908,320, 4,965,049, and 4,990,513, all of which are incorporated herein by reference.

In accordance with the present invention, a module group such as the module group 64 includes a plurality of modules 68. More particularly, the modules 68 include a reagent pump A module 70, a reagent pump B module 72, a reagent crane A module 74 and a reagent crane B module 76. All of the modules 68 are included in a serial communications loop 78 that establishes communication between the modules 68 and the multiple module controller 56. Each of the modules 68 shares a common functional design, a common communications means via the loop 78 with the controller 56, and all derive power from the bulk power supply 52.

Figure 2:
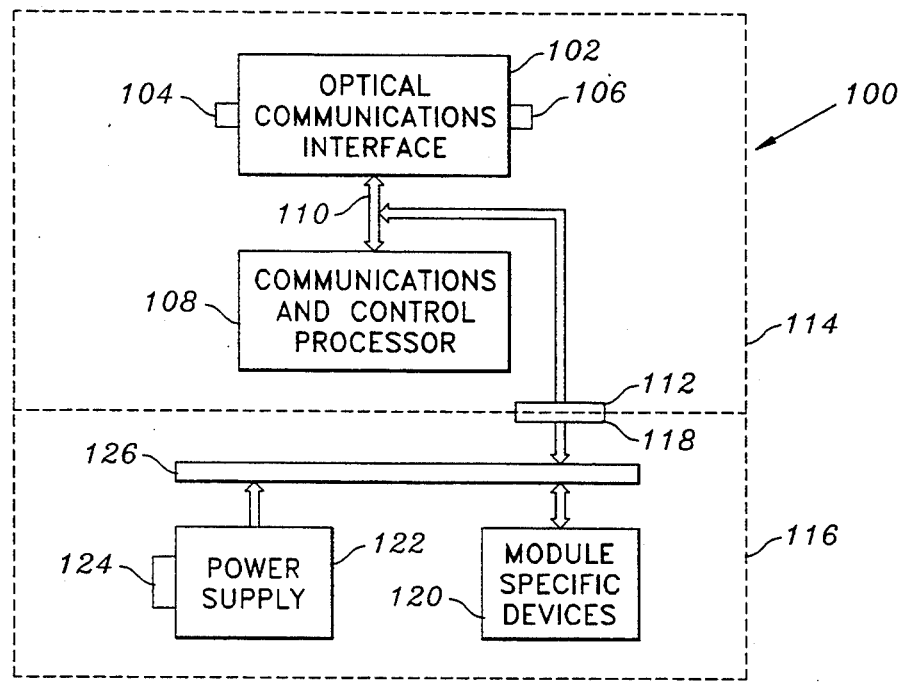
FIG. 2 is a block diagram of a module in accordance with the present invention suitable for use in the analyzer of FIG. 1.

More particularly, and with reference to FIG. 2, a typical module 100, which is applicable to all of the modules 68, includes an optical communications interface 102 that includes a serial optical communications input connector 104 and a serial optical communications output connector 106. The input and output connectors 104, 106 are adapted to connect the module 100 into an optical serial communications loop which may be, for example, the loop 78 of FIG. 1.

Continuing with FIG. 2, the optical communications interface 102 is connected with a communications and control processor 108. The optical communications interface 102 and the communications and control processor 108 may be connected by means of a bus 110 which is in turn connected to a suitable interface unit such as a connector 112. Preferably, the optical communications interface 102, communications and control processor 108, bus 110 and connector 112 are included in a common submodule (CS) 114 that may be shared among various forms of the typical module 100.

To complete the module 100, a function specific submodule (FSS) 116 includes a suitable interface such as a connector 118 adapted to connect with the connector 112 of the CS 114. The FSS 116 also includes function specific devices 120 that are specific to the particular function to be performed by the module 100. The FSS 116 also includes a power supply 122 which includes a connector 124 that may be connected to a common power source such as, the bulk power supply 52 in FIG. 1. A bus 126 provides common connection between and among the connector 118, function specific devices 120 and the power supply 122.

Thus, the typical module 100 provides a consistent functional design, allowing the typical module 100 to be adapted to a wide variety of functions within the automated analyzer 44. The typical module 100 provides a consistent functional design for the modules 68, as well as modules within the module groups 58, 60, 62 and 66.

Preferably, in utilizing an optical communications interface 102, data and program transfer between modules of the analyzer 54 is electrically isolated and thus not subject to noise and other difficulties common with, in particular, multi-line bus oriented architectures. Also, by providing a local power supply 122 in the typical module 100, power distribution throughout the analyzer 44 is considerably simplified, again reducing the possibility of module-to-module interference. Furthermore, the typical module 100 provides an easily re-configurable and individually testable module that helps assure that once the module 100 is placed into the analyzer 44, the module 100 will perform as tested.

Figure 3:
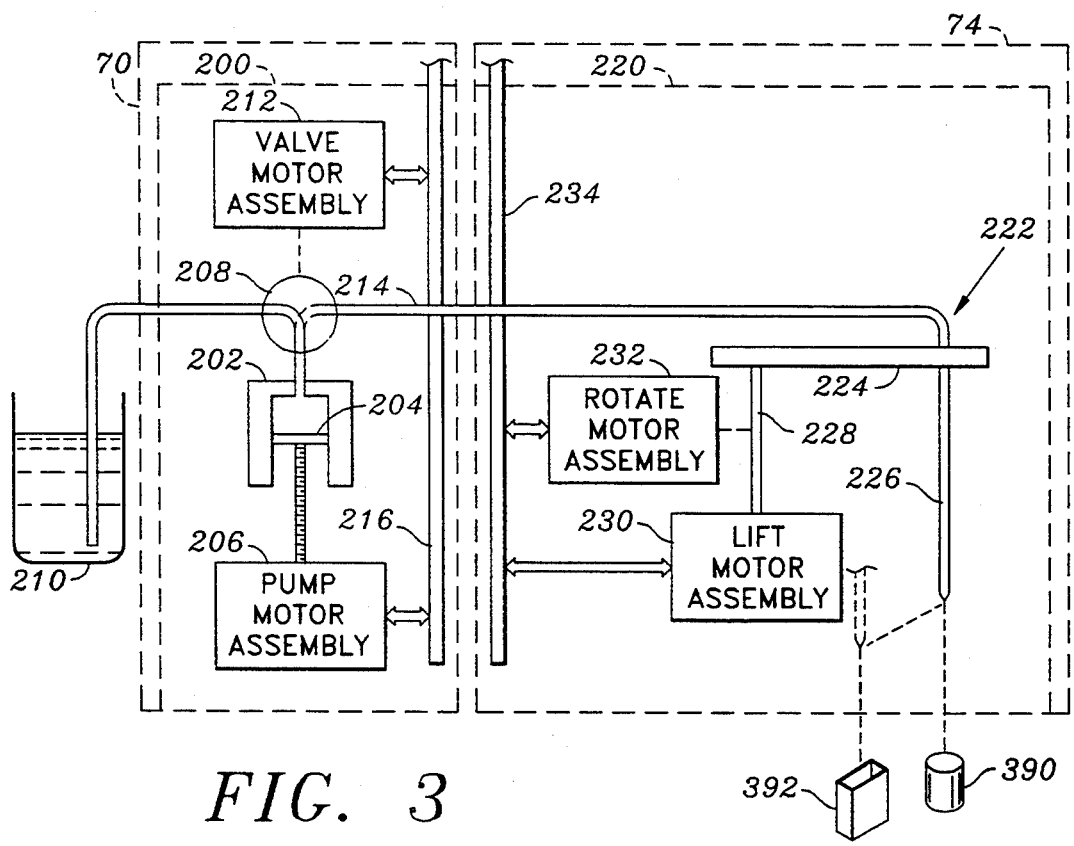
FIG. 3 is a functional diagram of function specific devices suitable for configuring the typical module of FIG. 2 as a reagent pump and probe crane modules.

To configure the typical module 100 for a particular functional or purpose within the automated analyzer 44, the function specific devices 120 are selected for the particular function to be performed by a given module. For example, FIG. 3 illustrates function specific devices for reagent pump A 70 and reagent crane A 74 of FIG. 1. With reference to FIG. 3, reagent pump A 70 function specific devices 200 configure the reagent pump A module 70 to provide valving and pumping for the delivery of reagent and washing water to a reagent probe. The devices 200 include a pump 202 having a plunger 204. The plunger is connected to a pump motor assembly 206. The pump motor assembly 206 drives and senses the position of the plunger 204.

The fluid port of the pump 202 is connected to a rotary valve 208 which in a first position illustrated by solid lines in FIG. 3 connects the pump 202 to a source of washing water such as a water reservoir 210. The valve 208 is mechanically connected to and under the control of a valve motor assembly 212 which drives and senses the position of the rotary valve 208. Under the control of the valve motor assembly 212, the valve 208 may be rotated to a second position, illustrated by dashed lines in FIG. 3, connecting the port of the pump 202 out of the module 70 via conduit 214. The pump motor assembly 206 and the motor valve assembly 212 connect to and are in communication with a bus 216 corresponding to the bus 126 of FIG. 2.

Continuing with FIG. 3, the conduit 214 provides fluid communication to function specific devices 220 of the reagent crane A 74. As with the reagent pump A 70, the reagent crane A module 74 block diagram is that of the typical module 100, with the function specific modules 120 being in particular the device specific modules 220 to thereby implement a reagent crane function.

More particularly, the reagent crane A module 74 includes a reagent crane 222 including an ann 224 and a fluid probe 226. The fluid probe 226 is in fluid communication with the conduit 214 and is open at its tip. The other end of the ann 224 is suspended by means, for example, of a rod 228. The rod 228 is supported by a lift motor assembly 230 and a rotate motor assembly 232. The lift motor assembly 230 vertically displaces the rod 228, thereby lifting the reagent crane 222. Similarly, the rotate motor assembly 232 rotates the rod 228 and senses the rotational position of the rod 228, thereby rotating the reagent crane 222 about the rod 228. The lift motor assembly 230 and rotate motor assembly 232 are in communication with a bus 234, corresponding to the bus 126 of the typical module 100 (FIG. 2).

Thus, it is seen that the typical module 100 of FIG. 2 can be adapted to specific functions by means of the function specific devices 120 and may be, for example, pumping and valving devices as with the function specific devices 200 of the reagent pump A module 70, or may be adapted to a reagent crane as illustrated with respect to the function specific devices 220 of the reagent crane A module 74. However, although the modules 70 and 74 perform different functions, the modules 70 and 74 share considerable common functions as illustrated with respect to the typical module 100 in FIG. 2, thus simplifying and expediting design, system integration, manufacture and servicing of the automated analyzer 44.

Preferably, for a motion control modules such as the modules 68, the modules include suitable programming to generate motor trajectories, to drive the motors, and to establish servo loop if necessary, for motion control. By grouping these control functions into the modules 68, the multiple module controller 56 is not concerned with the detail of motion control within the modules 68, and instead provides higher level motion timing for all of the modules 68. Similarly, with the multiple module controllers 54, 56 handling motion timing, that is, the details of the typical timing defined by timing diagrams for automated analyzers as is well known in the art, the instrument control computer 50 takes on the next higher level task, that is, scheduling of tests to be performed by the automated analyzer 44. Finally, the operator interface computer 42 provides a next higher and upper level for the operation of the automated system 40, handling input and output from a user of the system 40, as well as the host computer 48.

Preferably, as seen in FIG. 1, modules performing relating functions are grouped together within a module group. For example, the modules 68 aspirate and dispense reagent from a reagent container 390 into reaction cuvettes 392 on, for example, a reaction wheel (not shown). Two reagent pumps and cranes are provided to allow the simultaneous aspiration and dispensing of two reagents, for example, for a single chemistry where multiple reagent components must be combined or, for example, reagents for two different chemistries may be delivered to two locations on a reaction wheel. For the automated analyzer 44, the multiple module controller 54 may control the parallel analysis portion of the analyzer 44, or the multiple module controller 56 may control the serial analysis portion of the analyzer.

Figure 4:
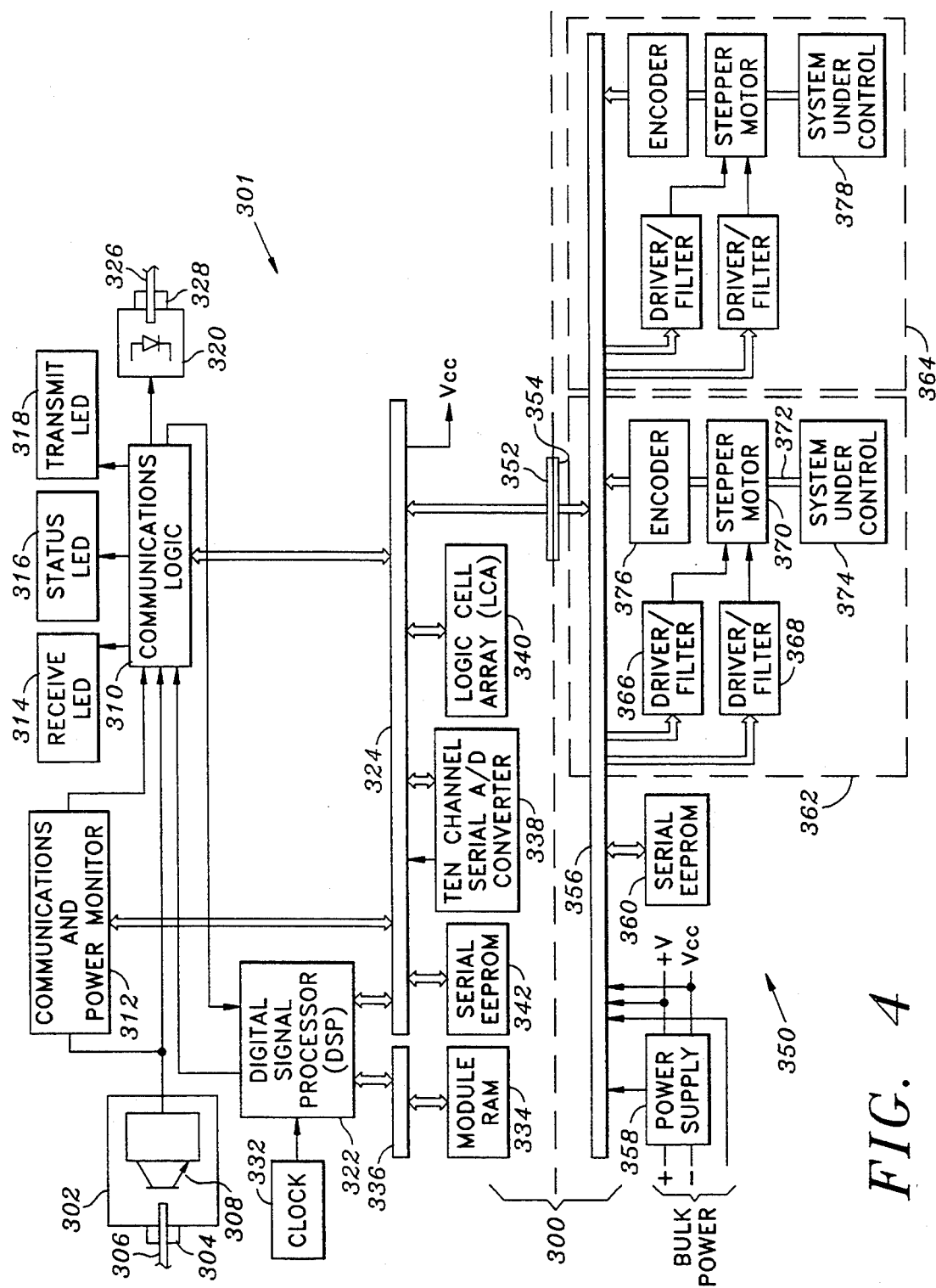
FIG. 4 is a block diagram of a two motor module in accordance with the present invention.

Preferably, the multiple module controller 56 is identical in block diagram to the typical module 100 of FIG. 2, provided that the function specific devices 120 of the typical module 100 include a plurality of optical communications interfaces adapted for connection to the communications loops with the module groups 62, 64 and 66. The communication loops established between the multiple module controller 56 and the module groups 62, 64 and 66 may be a Intel type 8051 nine bit protocol at a rate of approximately 20,000 to 500,000 bits per second and typically 100,000 bits per second in the present embodiment, and the communication link between the instrument control computer 50 and the multiple module controller 56 is an HDLC type protocol in a range of about 30,000 to 500,000 bits per second. The optical communications interface 102 preferably performs the communications interface for the link 80 between the instrument control computer 50 and the multiple module controller 56. Link 82 between the multiple module controllers 54 and 56 is a lower speed communications link, similar to the loop 78, although a higher speed HDLC protocol link may be used if higher communications speed is desired.

Where a module in a accordance with the present invention is used to drive and control two motors a detailed block diagram for such a module is seen with reference to FIG. 4. Such a module 300 includes a common submodule (CS) 301 including a fiber optic receiver 302 including a suitable fiber optic connector 304 for connecting to a fiber optic cable 306. A phototransistor 308 within the receiver 302 detects light from the cable 306, and the output of the fiber optic receiver 302 is applied to communications logic 310 and to a communications and power monitor 312. The communications logic 310 in turn provides outputs to a receive LED 314, a status LED 316, a transmit LED 318, a fiber optic transmitter 320 and digital signal processor (DSP) 322. Transmit data is also applied from the DSP 322 to the communications logic 310. The DSP 322 as well as the communications logic 310 are also connected to a common submodule (CS) bus 324 which provides power, data, address and signaling interconnections within the CS 301 of the module 300. It is to be recognized that while the processor 322 is identified as a digital signal processor, microprocessors may also be used according to the functional needs of the module 300.

The communications and power monitor 312 which may be a type MAX691 available from Maxim, monitors the output of the fiber optic receiver 302 and module power from the bus 324. An active communications input to the module 300 is indicated by the output of the fiber optic receiver 302 changing state, the normal state being light on. If an active communications input link is not sensed over a predetermined time period, for example, approximately 1.5 seconds, the communications and power monitor provides a reset output to the communications logic 310, as well as a reset to the DSP 322, forcing the DSP 322 into a reset process as described herein with respect to FIG. 6. Similarly, if the communications and power monitor 312 detects a power out condition, the monitor 312 provides a reset process interrupt to the DSP 322.

The communications logic 310 buffers the input from the fiber optic receiver 302 and applies the received data to the DSP 322. When a pass-through enable signal is received from the bus 324, the communications logic 310 passes all received data from the fiber optic receiver 302 to the fiber optic transmitter 320. The normal or usual operational condition of the module 300 is in a pass-through communications mode, and thus pass-through is generally enabled. Pass-through may be disabled, for example, for test or trouble-shooting conditions. Further, transmit data from the DSP 322 is applied to the communications logic 310 and is logically ORed with the receive data. The communications logic 310 also provides the receive data that is applied to the DSP 322 to the receive LED 314, the transmit data that is applied to the fiber optic transmitter 320 to the transmit LED 318, and a status signal from the DSP 322 via the bus 324 to the status LED 316. The status LED 316 may be used, for example, to blink troubleshooting messages, all under the control of the DSP 322.

The fiber optic transmitter 322 is connected to an output fiber optic cable 326 by means of a suitable connector 328. Thus, the input and output fiber optic cables 306 and 326, respectively, provide the optical serial communications loop to the module 300. Further, the optical communications interface 102 shown in block form in FIG. 2 may correspond generally to the fiber optic receiver and transmitter 302, 320, the communications logic 310, the communications and power monitor 312, and LEDs 314, 316 and 318.

A clock 332 generates a clock signal that is applied to the DSP 332. The DSP in turn generates a clock signal applied to the CS bus 324. Module RAM 332 is connected via a local data and address bus 336 to the DSP 322. By this arrangement the module RAM 334 is only accessible via the DSP 322.

A ten channel serial analog-to-digital (A/D) converter 338, logic cell array 340, and a serial electronically erasable programmable read-only memory (EEPROM) are connected to the CS bus 324. The A/D 338 includes an eleven channel analog-to-digital converter which provides a corresponding digital serial output to the bus 324. The A/D converter 338 may be used, for example, to monitor various analog levels within the module 300, providing data that may be transmitted by the module 300 to monitor normal operation of the module 300 as well as for diagnostic purposes.

The serial EEPROM 342 contains electronically alterable memory that may be output serially to the DSP 322 via the bus 324. Preferably, the serial EEPROM 342 includes data such as the CS 301 serial number, calibration data, module type, and if the module is a motion controller module, motor alignment information and the like. Advantageously, the use of the EEPROM 342 allows the module 300 as well as the CS 301 of the module 300 to provide specific data to a multiple module controller in control of the module 300. Data such as module serial number, calibration data, and the like can provide a detailed configuration status for an analyzer utilizing modules in accordance with the present invention. Other data may also be stored in the serial EEPROM 342, including, for example, serial numbers for the last several automated analyzers in which the module 300 was installed, module 300 as well as CS 301 serial numbers and manufacturing data, date of manufacture, and repair and/or maintenance history data.

The logic cell array (LCA) 340 is a programmable logic array device well known in the art and may be, for example, a type VC3042 from Xilinx. The LCA 340 implements miscellaneous logic functions required by the module 300 in a fashion that is well known and conventional in the art. The LCA 340 may include, for example, incremental decoder logic, miscellaneous input/output logic, and ports and logic for use by the serial EEPROM 342, all in a conventional fashion. The logic functions implemented by the LCA 340 may be implemented by other logic means, such as program array logic devices. However, because the LCA 340 is programmable, the use of the LCA 340 adds substantial adaptability to the CS 301 allowing the CS 301 to be used with various functions specific submodules.

Continuing with FIG. 4, the module 300 also includes a function specific submodule (FSS) 350. The FSS 350 is interfaced with, and connected to, the common submodule 301 via mating connectors 352, 354. The connector 352, part of the common submodule (CS) 301 provides a plurality of connections to the CS bus 324. The connector 354 is likewise connected to a FSS bus 356. The FSS 350 includes a module power supply 358, a serial EEPROM 360 and first and second motor assemblies 362 and 364 respectively.

The module power supply 364 receives bulk DC power from a bulk power supply, such as, for example the bulk power supply 52 of FIG. 1. The bulk power may be plus 36 volts DC and the DC return, for example. The power supply 358 in turn passes through filtered bus or bulk power +V that is applied to the FSS bus 356. The +V may be applied, for example, through the connectors 354, 352 and the CS bus 324 to one of the channels of the converter 338. The power supply 358 also generates regulated power Vcc for use throughout the module 300 which may be 5 VDC, and a current sense analog signal, both of which may be applied to separate channels of the converter 338.

The serial EEPROM 360 may be a device identical to the serial EEPROM 342 and is similarly used to store, for example, FSS 350 serial, calibration and other data as described above with respect to serial EEPROM 342, but all with respect to the FSS 350.

The first motor assembly 362 includes a phase A driver/filter 366, a phase B driver/filter 368, both of which provide filtered drive power to a stepper motor 370. The driver/filters 366, 368 may receive, for example, pulse width modulation signals generated by the DSP 322 to in turn drive the stepper motor 370. Preferably, the driver/filters 366 receive filtered +V from the power supply 358. The stepper 370 includes a shaft 372 connected to a system under control 374. The motor shaft 372 is also connected to a position encoder 376. The encoder 376 encodes the shaft 372 position and provides the encoded data to the FSS bus 356 which is in turn applied to the incremental decoder portion of the LCA 340. The driver/filters 366, 368, stepper motor 370, encoder 376 and the incremental decoder portion of the LCA 340 may be of conventional design and are well known in the art. Further, the system under control 374 may correspond, for example, to the pump 202 illustrated in FIG. 3. It is to be understood that while the module 300 is described as including an encoder 376 that provides high resolution information concerning shaft 372 rotational position, the encoder may be replaced by a more simple shaft position sensing means or no shaft position sensing means may be used depending on the particular function to be performed by the module 300. For example, a simpler shafter position sensing means could include a flag on the shaft 372 rotating through an inexpensive optical detector to provide a once per revolution position signal.

The second motor assembly 364 is essentially identical to the first motor assembly 362, driving a system under control 378 which may be, for example, the rotary valve 208 of FIG. 3.

In the embodiment disclosed herein, the digital signal processor 322 may be a type 320E14 available from Texas Instruments, the serial EEPROM 354, 360 may be a type 93C46 available from Hyundai, and the converter 338 may include a type ADC0811 available from National Semiconductor. However, other suitable choices will be readily apparent to those skilled in the art.

In operation, the modular system and method of the present invention may be illustrated with respect to the automated system 40. For example, an operator may select a test to be performed by using the operator interface computer 42. The operator may specify a particular sample by, for example, a sample identification number that may be bar coded onto the particular sample and may specify the particular test to be conducted. The operator interface computer 42 communicates the test request via the link 46 to the instrument control computer 50, which in turn schedules the various tasks to be performed by the automated analyzer 44. The test procedure may include, for example, drawing a reagent from a reagent container 390 and depositing the reagent into a reaction cuvette 392. With the reaction container 450 and reaction cuvette 452 appropriately positioned and the probe 226 initially positioned above the container 450, the multiple modular controller 56 transmits a serial command message via the loop 78 addressed to the reagent crane A 74. The optical communications interface for the module 74, illustrated generically as interface 102 in FIG. 2, receives the serial data comprising the message and provides the data to the communications and control processor 108. It is to be understood that the operation of the modules 70 and 74 is described with respect to the common submodule 114 illustrated in FIG. 2 and the pump and valve function-specific submodule 220 with respect to the reagent pump A 70, and the reagent crane function-specific submodule 220 of the reagent crane A module 74, both illustrated in FIG. 3.

The communications and control processor 108 for the module 74, in response to the command from the multiple module controller 56, lowers the probe 226 into the reagent container 450. With the probe 226 at its destination position within the container 450, the reagent crane A module 74 transmits a movement done message to the multiple module controller 56 via the serial loop 78. The multiple module controller 56 then transmits an aspirate control message to the reagent pump A module 70 which may include, for example, a predetermined trajectory for the pump motor assembly 206. The reagent pump A module 70 in turn controls the valve motor assembly 212 to connect the pump 202 to the conduit 214, controls the pump motor assembly 206 to draw reagent into the probe 226, then sending a command completed message to the multiple module controller 56.

The multiple module controller 56 continues to operate as just described, completing the reagent delivery cycle by withdrawing the probe 202, rotating the arm 224 to position the probe 226 above the reaction cuvette 392, lowering the probe 226 into the reaction cuvette 392, controlling the pump 202 to expel the reagent into the reaction cuvette 392 and withdrawing the probe 226 from the reaction cuvette 392. The multiple module controller 56 then commands the modules 70 and 74 to position the probe 226 within a probe wash station, adjust the valve 208 and operate the pump 202 to aspirate wash water into the pump 202 then again control the valve 208 and the pump 202 to expel the wash water through the interior of the probe 226 to wash the internal surfaces of the probe 226, while the external surfaces of the probe 226 may be washed by the probe wash station.

While the types of movements and actions performed by the reagent pump A module 70 and the reagent crane A module 74 are well known in the art, carrying out timing and movement profiles typical of automated analyzers, it is seen that the modules 70 and 74, in combination with the multiple module controller 56, create a unique system for the design, implementation, manufacture and maintenance of the automated analyzer 44. Commands are issued by the multiple module controller 56 to the modules 70 and 74, the modules 70 and 74 responding that they have successfully received the command. The modules 70, 74 interpret the commands, calculate trajectories, monitor the positions of the systems under control such as the valve 208, pump 202 and reagent crane 222. When the required motions have been completed, the modules 70, 74 communicate via the serial loop 78 to the multiple module controller 56, advising that the movement has been successfully completed.

Taking the reagent pump A module 70 as an example, the module 70 includes a control processor and associated hardware elements (for example, valve 208 and pump 202) to accomplish a well defined function, that is, reagent and wash liquid pumping. Thus, the physical boundaries of the module 70 are well defined, including the common submodule 114 and the function-specific submodule 116. Thus, the control processor logic and implementation directly corresponds to the hardware implementation of the module 70. The module 70 is also consistently interfaced with other functions in the analyzer 44 by means of the optical communications interface 102, which also provides electrical isolation of the communications path between functions in the analyzer 44. The local power supply 122 (FIG. 2) also further isolates the module 70, substantially reducing or eliminating interfunction power difficulties, such as power spikes, ground loops and the like. However, despite the isolation and integration of the module 70, considerable information and data concerning module configuration and performance is available, for example, by way of data that may be generated by the ten channel serial A/D converter 338 (FIG. 4) which may monitor +V, Vcc, power supply current sensing, as well as other representations of physical properties (temperature, humidity) that may be sensed within the module 70. Further, considerable information may be stored in the serial EEPROMs 324, 360, to fully characterize the submodules 301, 350.

Despite the highly integrated nature of the module 70, the typical module 100 which is the basis for modules within the module groups 58, 60, 62, 64 and 66 allows considerably varying functions to be readily adapted to the model presented by the diagram of FIG. 2. For example, a bar code reader may be the function-specific device 120. Typically, such bar code readers are obtained as a unit from a vendor for incorporation into the automated analyzer 44. Because the power supply 122 and the bar code reader, part of the function-specific devices 120, are both included in the function-specific submodule 116, the power supply 122 may be specifically designed to accommodate the needs of the bar code reader. Similarly, such a bar code reader may include a serial interface, such as RS-232 or RS-485 serial transmission standards, or may include a parallel data interface. In any event, such an interface may be applied to the FSS bus 126 through the connectors 112, 118 to the common submodule 114. There, the communications and control processor 108 (FIG. 2) which may include the DSP 322 and LCA 340 (FIG. 4) may be readily adapted to accommodate the input and output data and control needs of the bar code reader. It will be appreciated that the function-specific devices 120 may include RS-232 or RS-485 serial interfaced devices if the DSP 322 does not accommodate such serial standards.

Another form of a module according to the present invention is a temperature control module. Resistive heating elements or Peltier heating and cooling solid state devices may be included in the function specific devices 120, along with suitable drivers and controllers, all under control of the communications and control processor 108.

For each of these examples, it should be noted that the common submodule 114 (FIG. 2) and 301 (FIG. 4) may be used consistently from module-to-module or, as an alternative, several such modules with varying processor capacity by the selection of an appropriate DSP 322 may be designed for a broad range of uses within the analyzer 44 and in other similar analyzers. Furthermore, by providing a consistent electrical, electronic, mechanical and logical boundary between the common submodule 114 and the function-specific submodule 116, as well as an equally consistent electrical, electronic, mechanical and logical boundary between the modules 68 and multiple module controller 56, portions of the module 100 can be easily updated and modified to take advantage, for example, of the decreasing DSP 322 costs and increasing performance. Further, the module 100 allows a "mix-and-match" design and manufacturing approach to the completed module 100, allowing the common submodule 114 to be designed and manufactured separately from the function-specific submodule 116, yet enabling these modules to be easily and readily connected to enable, for example, DSP 322 computer program development and LCA 340 programming.

Although the particular motor control techniques in a motion control module such as the module 300 may be of a conventional design, a preferred form of trajectory control is illustrated with reference to FIG. 5.

Figure 5A:
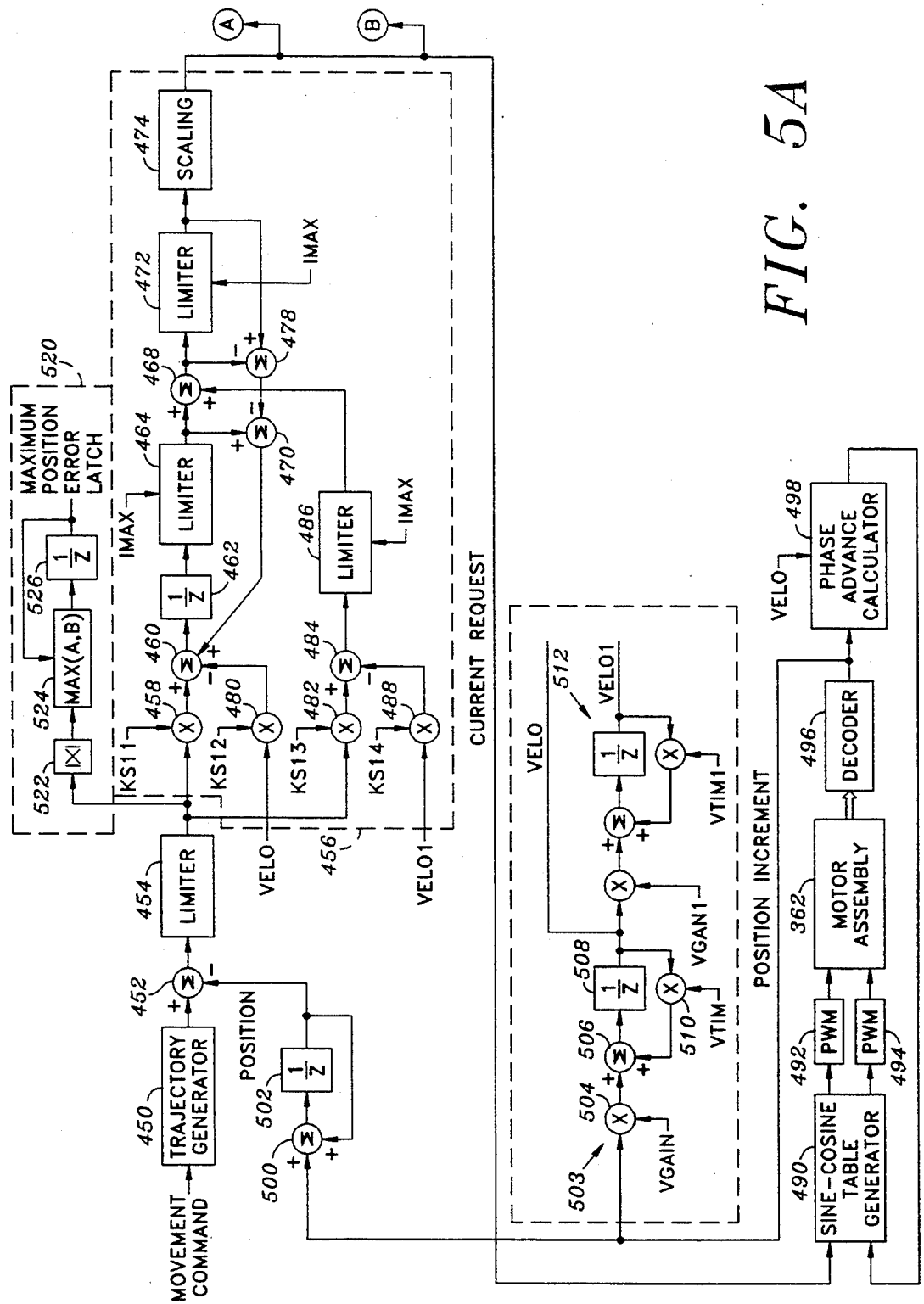
FIGS. 5A and 5B are functional logic diagram of the motor driver portion of a module in accordance with the present invention.
Figure 5B:
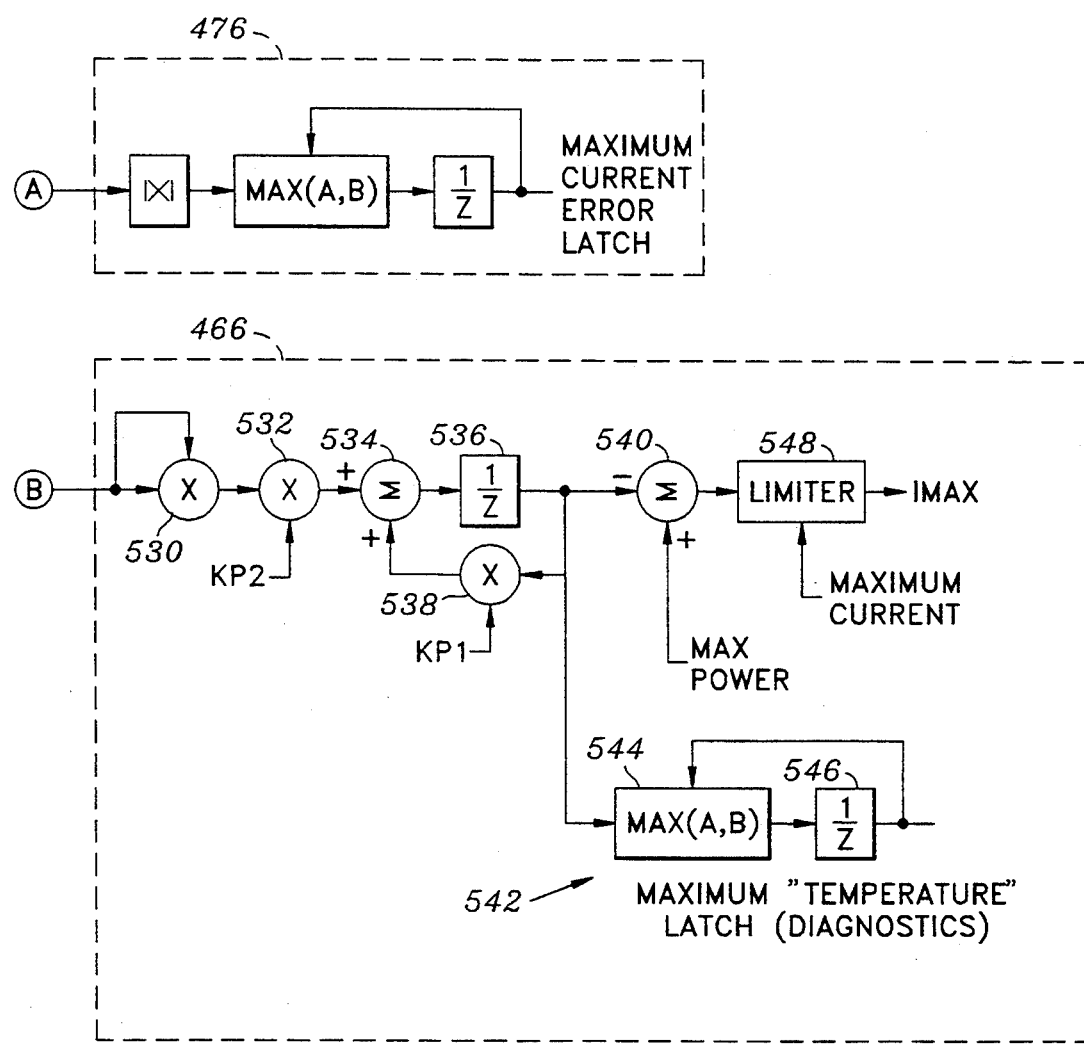
Figure 6A:
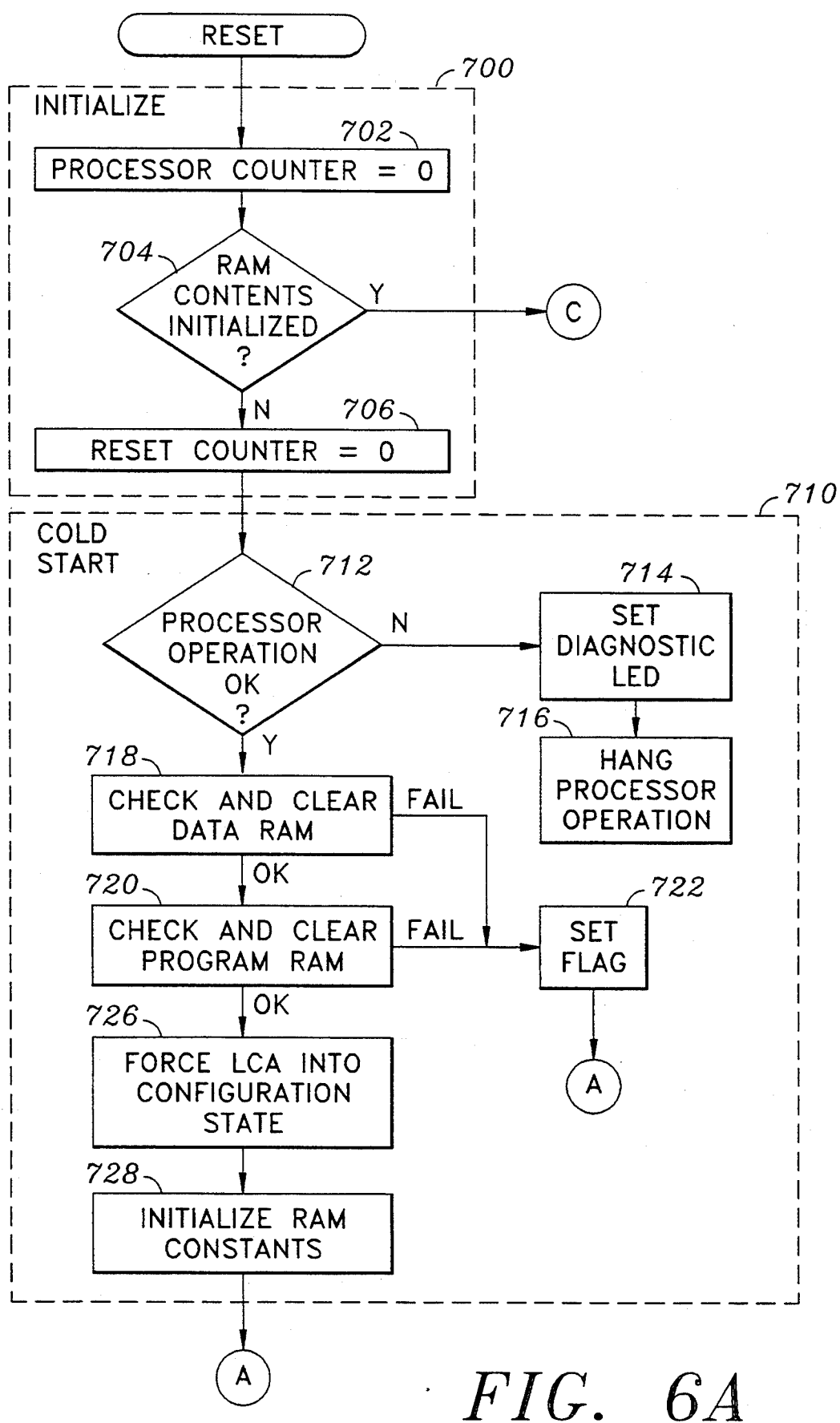
FIGS. 6A through 6E are diagram of the reset and communications initiation procedure performed by a module in accordance with the present invention.
Figure 6B:
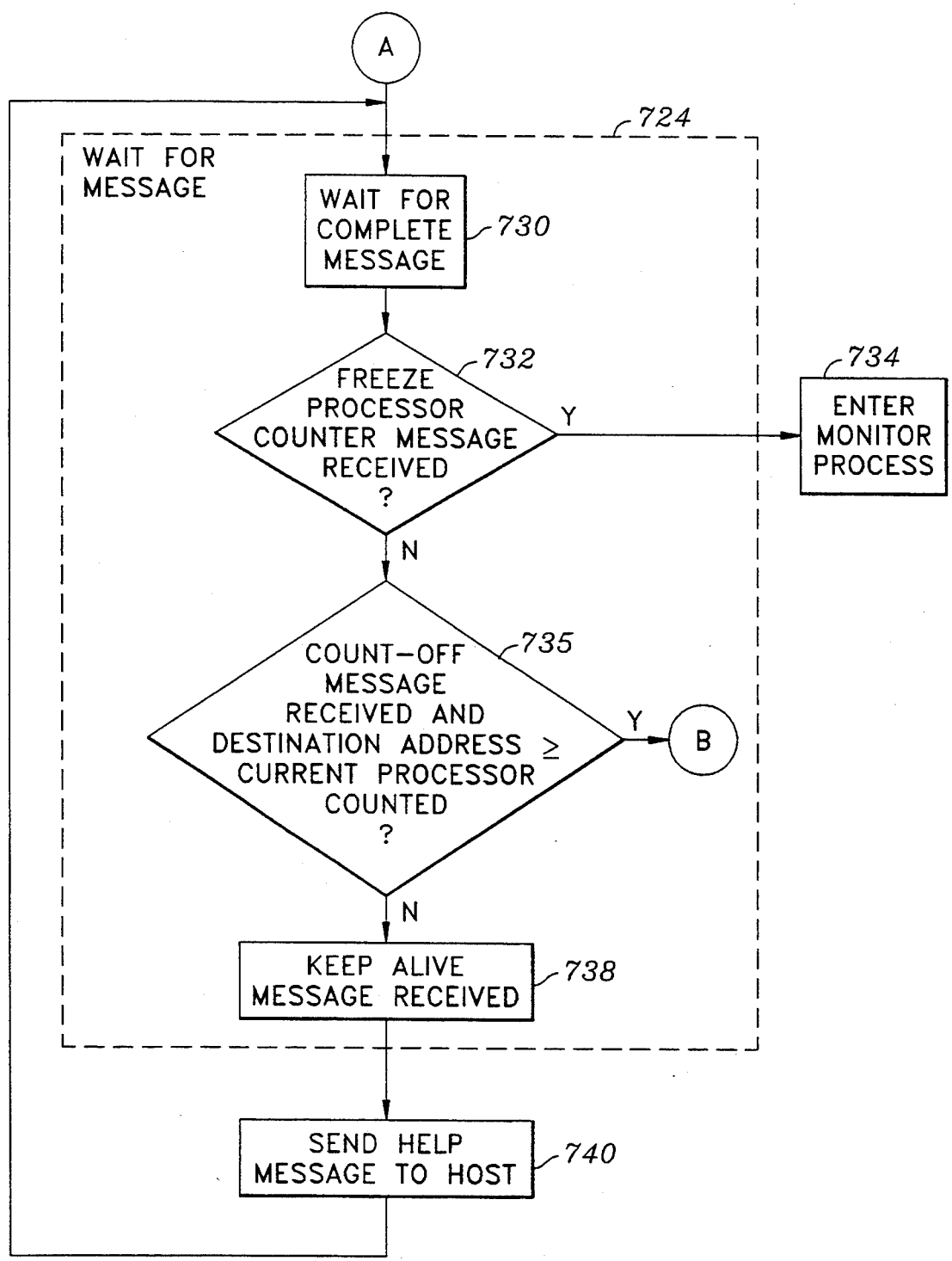
Figure 6C:
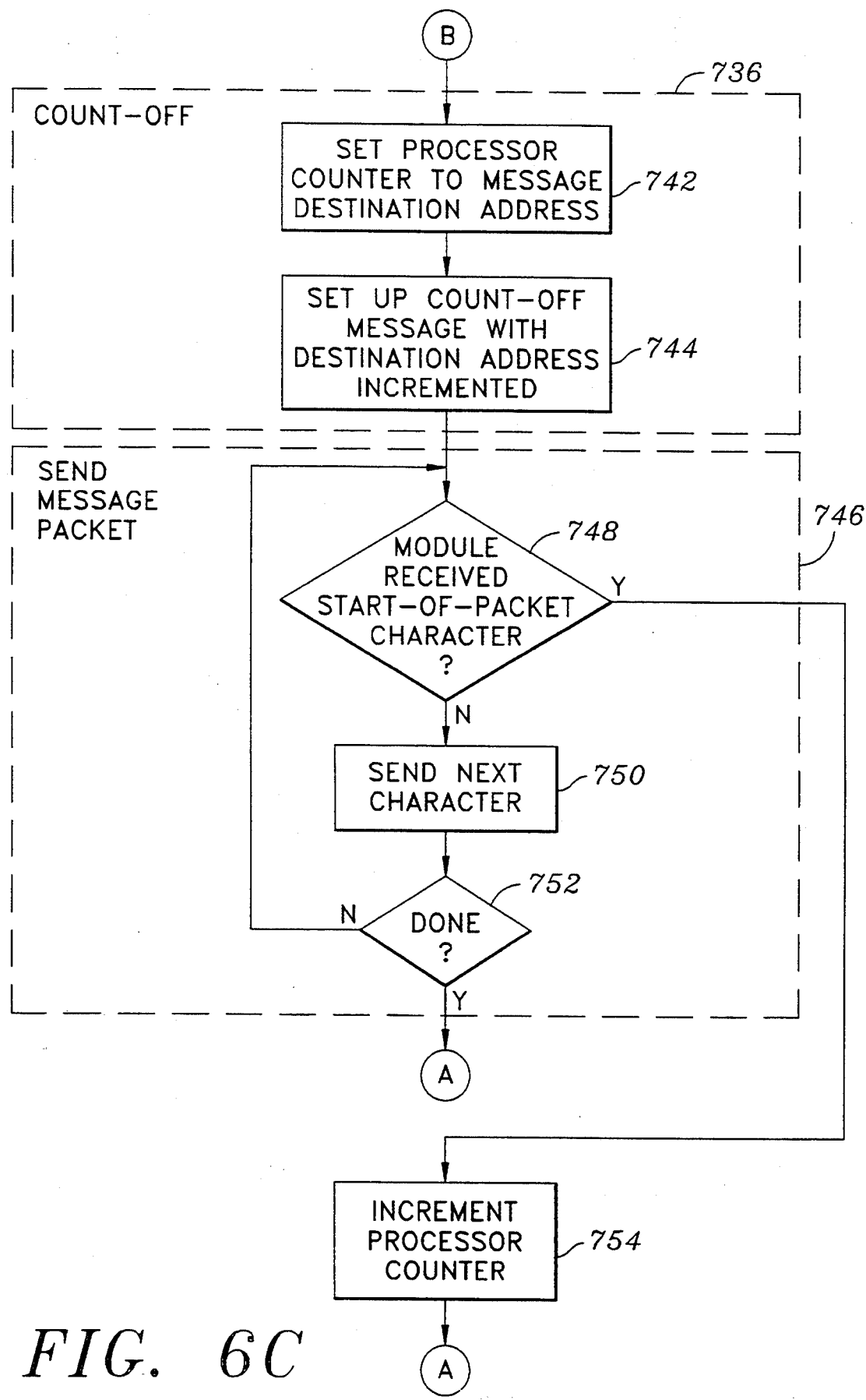
Figure 6D:
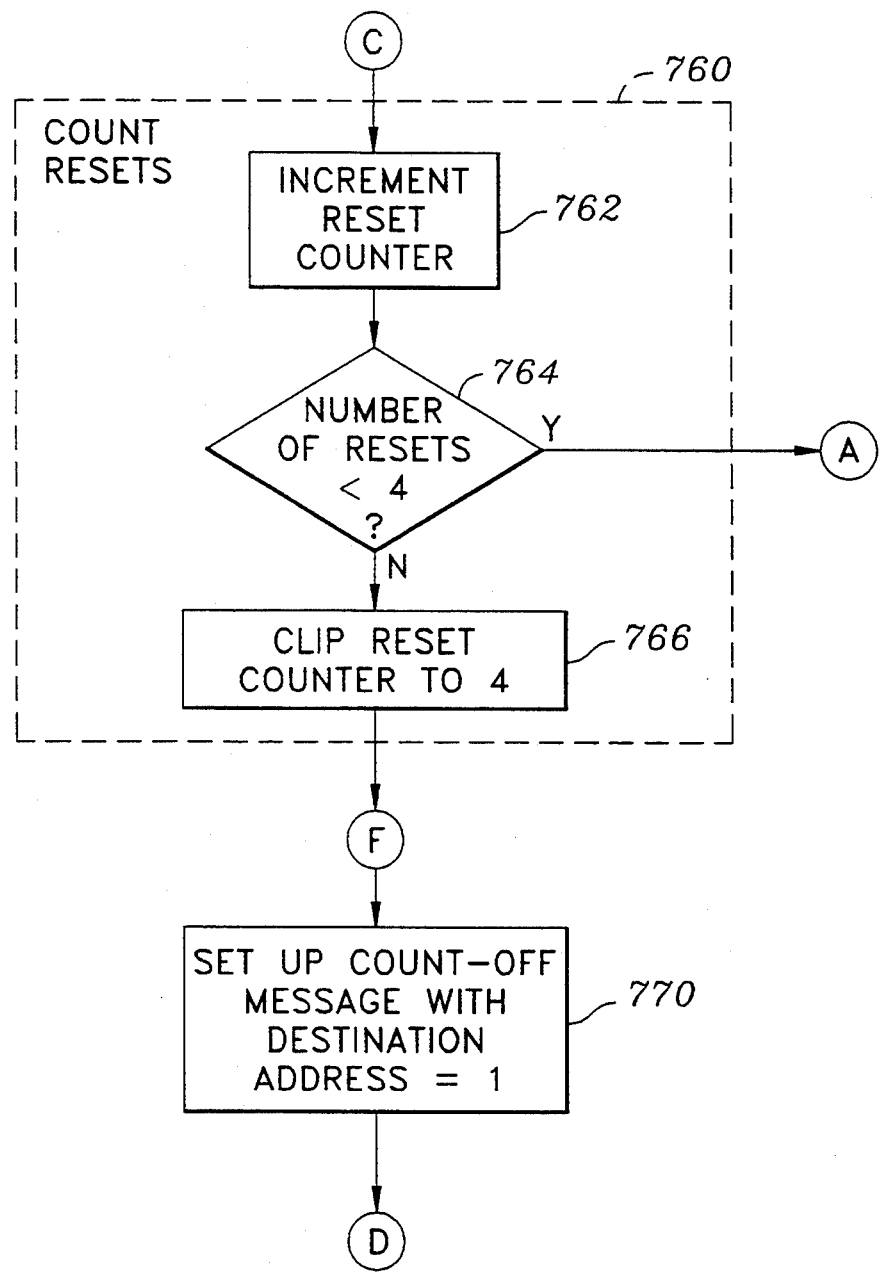
Figure 6E:
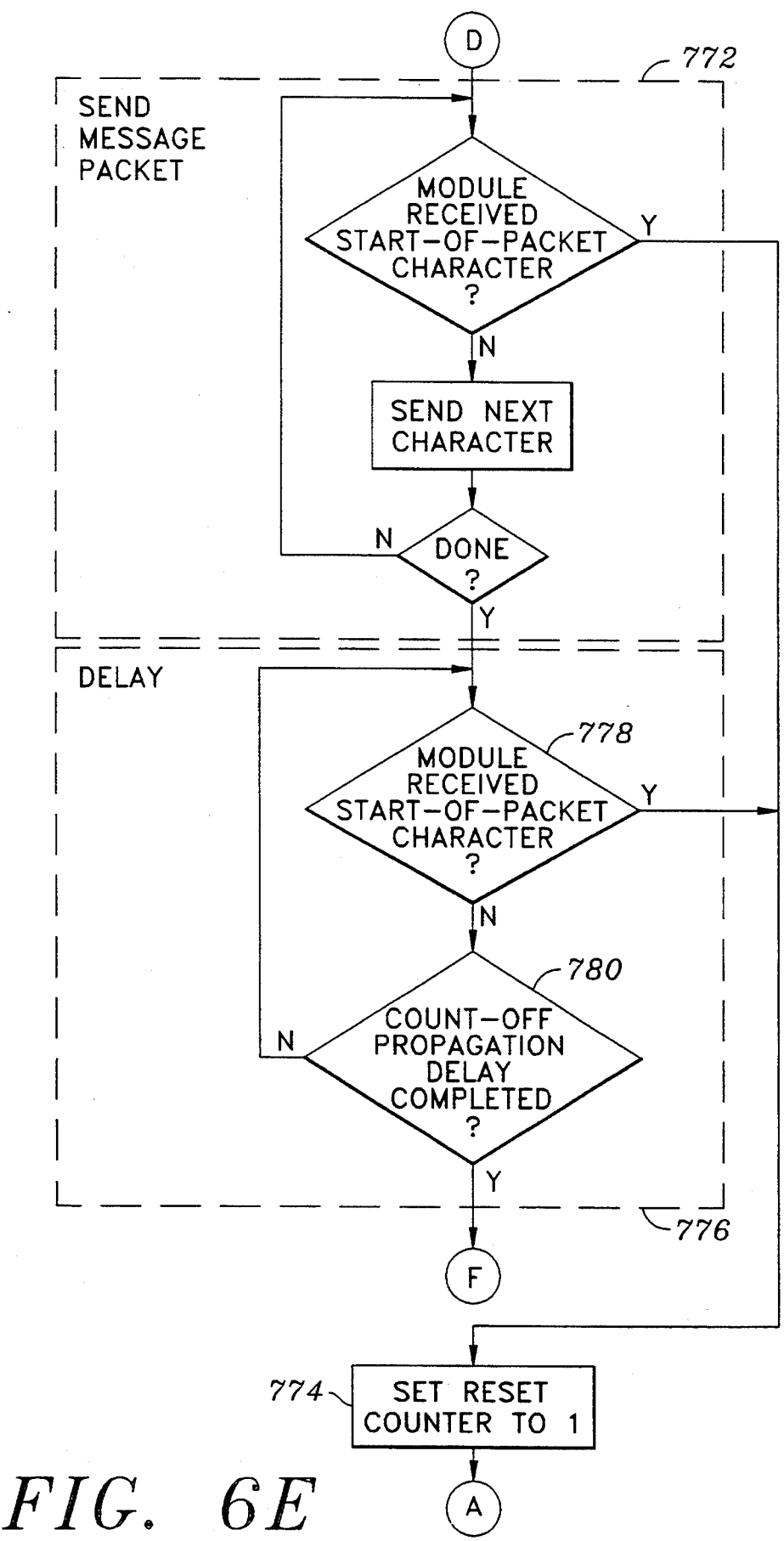

It is to be appreciated that FIG. 5 is essentially a logic diagram of the motor control functions implemented by programming of the DSP 322 and by programmed logic contained with the LCA 340, all of which will be readily apparent to those skilled in the art according to the logic illustrated in FIG. 5. The functions illustrated in and described with respect to FIG. 5 are performed, for example, during a control cycle. A control cycle is typically a cycle through the logic of FIG. 5 during which the logic functions are performed and values are updated. A one control cycle delay illustrated in FIG. 5 with "1/Z" indicates that the input is delayed one control cycle and then applied to the output as is conventionally known in the art. Different portions of the logic of FIG. 5 may have different control cycle periods. For example, a control cycle with respect to the motor assembly 362 and a decoder 496 may begin with the periodic sampling of the motor shaft 372 (FIG. 4) position as sensed by the encoder 376 every 240 microseconds. Other portions of the logic of FIG. 5 may cycle less frequently such as every two or three control cycles of the motor assembly 362 and decoder 496 as appropriate for control of the motor assembly 362.

With reference to FIG. 5, a desired motion profile and ending position is input to a trajectory generator 450 from, for example, the multiple module controller 56 via the loop 78. The trajectory generator 450 in turn generates a corresponding velocity profile and, from such a velocity profile, a target shaft position with respect to each control cycle over the time period projected for the movement. The output of the trajectory generator 450 in the form such target positions is applied to a summing node 452. Unless otherwise stated, all inputs to summing nodes described with respect to FIG. 5 are to a non-inverting input of such summing nodes. The difference between the desired or target position and the actual position of the shaft 372 (developed as is described hereinbelow) is calculated in the summing node 452 and is applied as a position error signal to a limiter 454. The limiter 454 limits the position difference to some predetermined value which, for normal and expected operation of the module 300, should be well above any position error value developed within the summing node 452.

The output of the limiter 454 is applied to a control loop 456. Generally, based upon the velocity of the shaft 372 and the difference between desired and actual position from the limiter 454, the control loop 456 generates a current request.

More particularly, the output of the limiter 454 is applied to a scaling multiplier 458 which multiplies the input by a predetermined scaling constant KS11, the output of which is applied to a summing node 460. The constant KS11, as well as other control and scaling constants described with respect to FIG. 5, may be determined experimentally or through analytical techniques such as root locus analysis. The output of the summing node 460 is applied to an integrating one control cycle delay 462, the output of which is applied to a limiter 464. The limit applied to the limiter 464 is IMAX, generated by a motor current function 466. The output of the limiter 464 representing the integral term in the control loop 456 is applied to two summing nodes 468 and 470. The summing node 468 sums the integral term output from the limiter 464 with a proportional term and the summing node 470 feeds back the output of the limiter 464 to the node 460, closing the integral term integrating loop.

The output of the summing node 468 is applied to a limiter 472, the limiting input of which is also the signal IMAX, and to an inverting input of a summing node 478. The output of the limiter 472 is applied to the node 478 and to a scaling function 474, the output of which is the current request signal that is applied to the motor current function 466 and a maximum latch 476. The difference developed at the output of the node 478 is applied to an inverting input of the summing node 470.

An anticipation term is developed by a first velocity signal VELO that is applied to a scaling multiplier 480 where the velocity signal VELO is multiplied by a constant KS12, the output of the multiplier 480 being applied to an inverting input of the summing node 460.

A proportional term feed-forward function within the control loop 456 begins with the output of the limiter 454 applied to a scaling multiplier 482 to which a constant KS13 is also applied. The output of the multiplier 482 is applied to a summing node 484, the output of which is applied to a limiter 486. A second velocity signal VEL01 is applied to a scaling multiplier 488 to which is applied a constant KS14. The output of the multiplier 488 is applied to an inverting input of the summing node 484. The limiting signal applied to the limiter 486 is also the IMAX signal, the output of the limiter 486 in turn being applied to the summing node 468.

Continuing with the overall description of FIG. 5, the current request signal from the scaling function 474 is applied to a sine-cosine table generator 490 which generates control signals applied to pulse width modulators (PWM) 492, 494. The modulators 492, 494 in turn provide controlling pulse width modulated signals to, for example, the motor assembly 362 (FIG. 4). The encoder output from the motor assembly 362 is applied to a decoder 496 that generates the position increment signal representing the accumulated shaft 372 position change from the prior control cycle. The position increment signal is applied, along with the VELO signal, to a phase advance calculator 498, the output of which is in turn applied back to the sine-cosine table generator 490.

The position increment signal is also applied to a position calculator including a summing node 500, the output of which is applied to a one control cycle delay 502. The output of the delay 502 is applied back to another input of the summing node 500, and is applied to an inverting input of the summing node 452. The output of the summing node 502 thus represents the cumulative or integrated position difference, or position, of the shaft 372.

The position increment signal, which represents an unfiltered form of velocity, is also applied to a first velocity filter including a scaling multiplier 504, the other input of which is a consistent VGAIN. The output of the multiplier 504 is applied to a summing node 506, the output of which is applied to a one control cycle delay 508. The output of the delay 508 is applied through a scaling multiplier 510 which scales the input by a constant VTIM. The output of the scaling multiplier 510 is supplied to the other input of the summing node 506. The output of the delay 508 is the signal VELO and is a filtered form of the position increment signal, thus better approximating the velocity of the shaft 372. The VELO signal is also applied to a second velocity filter 512 implemented identically to the velocity filter 503, but utilizing constants VGAIN1 and VTIM1 as constants. The output of the second velocity filter 512 is the VELO1 signal and is a further filtered approximation of velocity of the shaft 372.

The output of the limiter 454 is also applied to a maximum position error latch 520. Within the latch 520, the output from the limiter 454 is first applied through an absolute value function 522, and in turn to a maximum select function 524. The output of the maximum select function 524 is applied through a one control cycle delay 526, the output of which represents the maximum position error latch output and also which is applied to the other input of the maximum select function 524.

The output of the scaling function 474, representing the current request applied to the sine-cosine table generator 490 is also applied to the motor current function 466. The input to the motor current function 466 is first squared and multiplied by a constant KP2 by way of multipliers 530 and 532. The output of the multiplier 532 is applied to a summing node 534, the output of which is applied to a one control cycle delay 536. The output of the delay 536 is applied back through a multiplier 538 to the other input of the summer 534, and is applied to an inverting input of a summing node 540. The output of the delay 536 is also applied to a maximum "temperature" latch 542 including a maximum select function 544 and a delay 546. A maximum power constant is applied to the summing node 540 and the output of the summing node 540 equal to the difference between short term average power dissipated by the motor 370 is applied to a limiter 548, the output of which is IMAX. The limiting input to the limiter 548 is a torque (current) limit for the notor under control in the motor assembly 362. The limiters 454, 464, 472, 486 and 548 are bipolar, in essence applying the same sign to the limit values as are the signs of the input values, because the input values to the limiters may be both plus and minus, representing the two directions of motor motion and the corresponding bipolar nature of the current request signal.

In overall operation of the motor control function illustrated in FIG. 5, the trajectory generator 450, node 452 and limiter 454 operate to provide the position error signal to the control loop 456. The position error signal, as modified by the constant KS11, is reduced at the node 460 by the anticipation term value. The sum of the integral and proportional terms developed at the output of the summing node 468 is limited by the limiter 472, placing a maximum magnitude limit on the current request signal. Advantageously, the limiter 472 and summing node 478 apply the amount by which the output from the node 468 exceeds the IMAX value to the inverting imput of the node 470, part of the integrator term loop. This novel feedback and reduction of the integrator term loop value helps to stabilize the control loop 456 and thus the motor assembly 362 and provides an integrator anti-windup function. The limiters 464 and 486 also provide direct limiting of the integral and proportional terms, respectively, further enhancing the performance of the control loop 456.

The motor current function 466 models the power consumed by the motor 370 and thus the temperature of the stepper motor 370 by calculating the $I^2R$ heating and environmental cooling of the stepper motor 370 in response to the current request signal. The $I^2R$ calculation is performed by the multipliers 530 and 532 with a suitable value of R supplied by the system variable KP2. The delay 536, multiplier 538 and summing node 534 form a filter approximating a leaky integrator and thus filter the output from the summing note 534 and produce an output related to the short term average power dissipated by the motor 370 and thus the motor 370 temperature. The output of the delay 536 is latched through the maximum temperature latch 542.

As the output of the delay 536 increases, indicating increasing power dissipation and motor temperature, the difference from the node 540 decreases, decreasing the IMAX value and limiting the current request signal through action of the IMAX value in the loop 456. Advantageously, this allows a short term maximum torque of the stepper motor 370 to be significantly higher than the sustainable torque from the motor 370 without overheating the motor 370. It also enables the stepper motor 370 to be initially started at a fixed maximum current and resulting torque which is reduced with time to limit the time averaged power to the motor. This feature of the present invention allows the stepper motor 370 to develop the higher torque frequently associated with acceleration or deceleration while running at a lower torque during a constant speed portion of a velocity profile without overheating. Because stepper motors in general have a relatively large thermal time constant, such a feature enables wide motor torque performance within the velocity profile often required of stepper motors. Also with this feature the motor does not overheat when, for example, a mechanical fault that may produce a stalled condition and a sustained overload to the motor 368.

Lastly, the maximum current error latch 476 is implemented similarly to the latch 520 and provides a maximum current error latch output that may be reported by the module 300, along with the maximum position error latch 520 output and the maximum temperature latch 542 output, to, for example, the multiple module controller 56, thus providing a real-time and continuous monitoring of the motor operability and loads placed upon the module 300.

Various communication protocols and logical approaches may be used in implementing a communications loop for the modular system of the present invention. Preferably, all communications on such a communications loop, for example, loop 78 of FIG. 1, is via packets of data. For example, a packet may include a destination address, a source address, a message length, the message itself which may be data, commands or the like, and a checksum value. To indicate that a packet has been successfully received, the receiving module, such as the reagent pump A module 70, transmit an acknowledge packet which has a message length of zero, thus creating a relatively short and therefore quickly transmitted acknowledgment.

The communications on each such communication loop is preferably fashioned after a scheme compatible with the Intel type 8051 nine bit protocol, wherein an extra ninth bit is transmitted with each word, and separate from parity. The presence of a ninth bit ON in a word indicates that the word is the start of a packet. Any partial packet received by a module when a new start-of-packet word is received is ignored by the receiving module, thus providing a mechanism whereby any module along a communications loop, or a master module for that loop, can recover from a bad or incomplete packet.

Preferably, a master module, such as the multiple module controller 56 with respect to the reagent pump A module 70, sends a packet to the module 70. If for some reason that packet is not appropriately received or processed and thus acknowledged by the module 70, the controller 56, after some time-out period of, for example, one millisecond, resends the packet. The start of the new packet thereby cancels the incomplete prior packet held within the 70, re-establishing communications between the multiple module controller 56 and the module 70.

Communication with a module in accordance with the present invention is initialized by means of a reset process. The reset process may be entered, for example, on module power-up, if a module suffers a software failure, or if communications with a module is interrupted. The reset process includes a count-off identification sequence that identifies the modules on a communications loop and also serves to locate the location of a break in the communications loop, if such a break exits.

With reference to the reset process of FIG. 6 and assuming that the loop 78 of FIG. 1 includes the typical module 300 of FIG. 4, upon beginning the reset process, the module 300 enters an initialize state 700. Programming for the reset process of FIG. 6 may be stored in non-volatile memory on board the DSP 322. While in the initialize state 700, the DSP 322 sets a processor counter variable to zero (step 702) and checks to see if the RAM 334 contents have been initialized (step 704). If initialization contents are stored within RAM 334, then the module has already undergone a cold start procedure. If the RAM 334 contents are not so initialized, as would occur during a power-up reset process, then the DSP 322 initializes a reset counter variable to zero (step 706) and enters a cold start state 710.

In the cold start state 710, the DSP 322 first verifies its own operation by performing a power-up self test (step 712) and, if not, lights diagnostic LED such as the status LED 316 (step 714) and hangs or loops the DSP 322 to thus suspend DSP 322 operation (step 716). If DSP 322 operation is okay (step 712), the DSP 322 then checks and clears data and program RAM (steps 718 and 720), both included in RAM 334. If either data RAM or program RAM fails, the check steps, the DSP 322 sets a flag (step 722) and proceeds to a wait-for-message state 724.

On the other hand, if data RAM and program RAM included in RAM 334 are functioning correctly, the DSP 322 then forces the LCA 340 into a configuration or programming state (step 726) and initializes RAM constants (step 728). When completed the module 300 exits the cold start state 710 and enters the wait-for-message state 724.

In the wait-for-message state 724, the DSP 322 first enters a wait for complete message state 730. When a complete message is received, the DSP 322 checks to determine if the message is a freeze processor count message (step 732). If so, the initialization or reset process of FIG. 6 is completed. The module 300 exits the initialization process and enters a monitor process 734.

If the message is not a freeze processor count message, the DSP 322 checks to determine if the message is a count-off message and if the destination number in the count-off message is greater than the current processor counter variable stored by the DSP 322. If so, the DSP 322 exits the wait-for-message state 724 and enters a count-off state 736.

If the message was not a count-off message with a destination number greater than the current processor counter variable, then a keep alive message has been received (step 738) and the DSP 322 exits the wait-for-message state 724 and enters a send help message state 740.

In the state 740, the DSP 322 sends a help message to the host module, in this example the multiple module controller 56, leaving it to the multiple module controller 56 to recognize that at least one of the modules within the communications loop 78 is in a reset process. The multiple module controller 56 may then poll the remaining modules on the loop 78 to determine which modules within the communications loop 78 are still correctly functioning and communicating and thereby identify the module requesting help. Once the help message is sent, the DSP 322 re-enters the wait-for-message state 724 to then wait for another message. One form of help that the multiple module controller 56 may provide is to command all of the modules on the loop 78 to initiate the reset sequence of FIG. 6.

In a reset process resulting from a power-up condition, and assuming that the communications loop 78 is operational, the overall approach is that the modules in a communications loop initially and automatically count-off to create an ascending processor identification number for each of the modules in the communications loop. For example, in the communications loop 78, on initial power-up all of the modules 68 enter the reset process and reach the wait-for-message state 724 as just described. To begin the count-off procedure, the multiple module controller 56 sends a count-off message packet with a destination address of one. This message is received by all of the modules 271. Each of the modules 271 thus at step 735 enter the count-off state 736.

In the count-off state 736, the DSP 322 sets the processor counter variable to the message destination address (step 742) and sets up a count-off message with the destination address incremented (step 744). The module then enters a send message packet state 746 in which the DSP 322 checks to determine if the module has received a start-of-packet character (step 748). If so, the module is not the first of the modules 68 and accordingly the module increments the processor counter variable (step 754) and returns to the wait-for-message state 724.

On the other hand, if a start-up packet character is not received (step 748), the DSP 322 sends the next character in the message packet (step 750) and checks to see if the entire message packet has been sent and thus it is done with the message packet (step 752). If not, the DSP 322 returns to step 748 and continues repeating the steps 748, 750 and 752 until either the complete message packet has been sent or a start-of-packet character is received as previously described.

If the entire message packet has been sent as determined in step 752, then the module has successfully transmitted its count-off message and the DSP 322 returns to the wait-for-message state 724.

The count-off procedure as just described would be that performed, for example, by reagent pump A module 70 within the modules 68. For a subsequent module in the serial communications loop 78, for example, the reagent pump B module 72, such a module would enter the wait-for-message state 724, and exit from step 735 to the count-off state 736. More particularly, the reagent pump B module 72 would enter its send message packet state 746, but would be interrupted by the count-off packet transmitted by the prior module in the communications loop 272, the reagent pump A module 70 as described above. Accordingly, a start-of-packet character is detected (step 748) and the increment processor counter variable step 754 is performed, incrementing the processor counter variable to, for example, two for the reagent pump B module 72.

Once the count-off message from the reagent pump A module 70 is completed, the reagent pump B module 72 determines that a count-off message has been received and that the destination address is greater than or equal to the current processor counter variable. This is so because the reagent pump A module 70 incremented the destination address from one to two and included that destination address in its count-off message. Accordingly, the reagent pump B module 72 enters the count-off state 736, setting its processor counter variable to the received message destination address of two and setting up a count-off response with the destination address incremented, that is, three.

The reagent pump B module 72 then enters the send message packet state 746. The reagent pump B module 72 will not be interrupted as it sends the message packet because the sample pump A module 70 has completed its count-off procedure and is in the wait-for-message state 724.

Similarly, a module further along the serial communications loop 78 within the modules 68 receives count-off messages (step 735), sets up a count-off message (step 736) and begins to send the message packet, only to be interrupted by the beginning of message packets (step 748) from prior modules in the communications loop 78. Each time this occurs the processor counter variable is incremented (step 754), returning the module to the wait-for-message state 724. Ultimately, the module is not interrupted by the receipt of a start-of-packet character while a count-off message is being sent (step 748), thus allowing the complete count-off message to be transmitted and returning the module to the wait-for-message state 724 where the module waits while the remaining modules in the communications loop 78 complete the count-off procedure.

For example, the reagent crane B module 76 will have its count-off message interrupted three times by count-off messages from the modules 70, 72 and 74, in that order, ultimately achieving a processor counter variable value of four.

Once the multiple module controller 56 has received count-off messages from all of the modules 68, the controller 56 checks to determine if the number of modules 68 for which the module controller 56 has received count-off messages equals the number of modules that should be in the loop 78 according to system configuration information provided, for example, from the instrument control computer 50. If so, the multiple module controller 56 sends a freeze processor counter variable message to each of the modules 68, specifying each module by processor counter variable value. When this message is received by a module in the wait-for-message state 724, the DSP 322 freezes the processor counter variable, using this value as the module destination address for further communications with the multiple module controller 56, exits the reset process of FIG. 6 at step 732, and enters the module monitor process 734.

The reset process of FIG. 6 also contemplates the possibility of a processor within a module experiencing a software fault and accordingly failing to operate correctly, or a break within the serial communications loop 78. If, for example, the DSP 322 experiences a software fault and accordingly fails to function correctly, a watchdog reset timer within the DSP 322 (not shown) times out, forcing the DSP 322 into the reset process via the initialize state 700.

The DSP 322, finding that the RAM contents have been initialized (step 704), enters a count resets state 760, incrementing the reset counter variable (step 762), checking the number of resets and, if less than four (step 764), entering the wait-for-message state 724. When the next complete message is received (step 730), the message will not be a freeze processor counter message nor will it be a count-off message (steps 732 and 735) because the modules 68 are not in a count-off procedure. Instead the message is considered a keep-alive message (step 738), that is, any message on the loop 78 from the controller 56 that is not addressed to the particular module, and the DSP 322 sends a help message to the host (step 740). The DSP 322 then returns to the wait-for-message state 724, awaiting the next message from the multiple module controller 56. The controller 56 may respond to the help message as described above.

If a fault should occur somewhere along the serial communications loop 68, the reset process of FIG. 6 also includes a method for identifying to the multiple module controller 56 where along the communications loop the fault occurred. For the purpose of this example, it is assumed that the communications loop between the reagent pump B module 72 and the reagent crane A module 74 has been broken or has otherwise been interrupted and rendered inoperable.

In such an instance, the module (in this example, reagent crane A module 74) enters the initialize state 700 as a result of the monitor 312 timing out. The timing period of the monitor 312, as described above with reference to FIG. 4, is restarted by any communications activity received via the receiver 302, indicating that the communications loop 78 is in good physical condition.

Preferably, the period of the monitor 312 is approximately 1.5 seconds. With the DSP 322 in the initialize state 700, the DSP 322 detects that the RAM constants have been initialized (step 704). The DSP 322 exits state 700 and enters a count reset state 760. There, the DSP 322 increments the reset counter (step 762) and checks the reset counter to determine if the total number of resets is less than four (step 764). If the number of resets is less that four, the process enters wait-for-message state 724 and waits for a complete message 730.

However, with the communications loop 78 open and non-functioning with respect to the reagent crane A module 74, the DSP 322 continues to wait for a message (state 730) until the monitor 312 again times out because it is not reset by any incoming data received at the fiber optic receiver 302. Accordingly, the DSP 322 again re-enters the initialize state 700, finds that the RAM constants are initialized (step 704), and enters state 760 incrementing the reset counter, checking the number of resets and if less than four, entering the wait-for-message state 724.

After four such cycles are completed, the DSP 322 determines that the reset counter is set to four. The DSP 322 enters step 766, clipping or resetting the reset counter to 4 and enters a count-off set-up state 770. The DSP 322 sets up a count-off message with a destination address set to one and enters send message packet state 772. The send message packet state 772 is logically identical to the send message packet state 746 and thus the DSP 322 begins to send the count-off message packet. Because the communications loop 78 is open and non-functioning with respect to the reagent crane A module 74, the DSP 322 will not receive a start-of-packet character, and thus will successfully transmit the count-off message packet, leaving state 772 and entering a delay state 776. In the delay state 776, the DSP 322 does not detect a start-of-packet character (step 778) because of the non-functioning communications loop 78 and accordingly completes a count-off propagation delay (step 780). The DSP 322 again enters the count-off set-up state 770 and continues to loop through the state 770, 772 and 776 unless communications is restored.

Thus, the reagent crane A module 74 is operating as a communications loop 78 master, that is the DSP 322 detects no other processors on the communications loop 78 and thus repeatedly sends a master count-off message packet indicating that it is processor 1, or the first processor in the loop after the communications break, and that it is in a reset process.

The next module in the communications loop 270 after the open portion of the loop is the reagent crane B module 76. The processor in the reagent crane B module 76 operates as just described with respect to the reagent crane A module 74, eventually entering the send message packet state 772. However, because the reagent crane A module 74 starts to send its message packet, the processor determines that a start-of-packet character has been received, thus exiting the send message packet state 772, setting the reset counter to 1 (step 774) and entering the wait-for-message state 724.

With the count-off message received from the reagent crane A module 74, the processor in reagent crane B module 76 detects a complete message (step 730) and that the message was a count-off message (step 735). Accordingly, the processor then executes state 736 to form a count-off message and sends the count-off message in state 746 but identifying the processor as number two.

Thus, the multiple module controller 56 receives count-off messages from two modules, determines that it is not receiving acknowledgments from any module along the communications loop 78 and takes an appropriate action, such as notifying the instrument control computer 550 and a loop failure has occurred, then attempting to restart the loop 78. The instrument control computer 50 then may, for example, initiate an orderly shut-down of the analyzer 50 processes while the multiple module controller 56 attempts to re-establish communications within the communications loop 78.

If the communications loop 78 is only momentary interrupted, but sufficiently long enough for the monitor 312 to begin the lost communications count-off sequence just described, then, when the communications loop 78 is restored, the module after the communications loop break exits the wait-for-message state 724 via the step 738, sending a help message to the host (step 740). Similarly, if the communications loop 78 is restored while the processor of one of such modules is in the state 772 or 776, the processor exits to step 774, resetting the reset counter variable to one, entering the wait-for-message state 724 and again sending a help message to the host as described above.

Thus, the count-off process of FIG. 6 provides a self-configuring system, that is, allowing the modules 68 to be arranged in any order along the communications loop 78, while providing a communications process that is complete with acknowledgments of received packets by each of the modules 78 and the controller 56. Further, the reset process of FIG. 6 operates to detect failures in the communication loop 78 as well as modules that have failed to function correctly due to processor programming errors, resulting in the processor becoming "lost".

As described above with respect to step 732, once a module processor has completed the count-off reset process of FIG. 6, the processor (and thus module) enters a monitor process 734. In the monitor process 734, the module processor responds to various monitor process commands from the multiple module controller 56. Examples of monitor process commands include:

Run Self Diagnostics: Verify DSP 322, RAM 334 and LCA 340, and report flags such as flag set in step 722.

Module Type: Determine module type (pump, thermal controller, etc.) hardware and programming revision number, module serial number and calibration data.

Modify EEPROM1: Modify the serial EEPROM 342 to update the identification of submodule hardware elements, modify calibration data, etc.

Modify EEPROM2: Modify the serial EEPROM 360 to update the identification of submodule hardware elements, modify calibration data, etc.

Download LCA Configuration: Download LCA 340 configuration data to thus configure LCA 340, from multiple module controller 56.

Download program RAM: Download program for storage in RAM 334 from multiple module controller 56.

Execute Downloaded Code: Jump to and initiate execution of downloaded program code stored RAM 334, thereby making available additional processes for the module.

Debug Mode: Set or reset a debug mode, enabling or disabling debug routines otherwise not available during normal operation of the module and thus the analyzer 44.

It is to be appreciated that the above commands are merely exemplary and are available through programming resident within the module that need not be downloaded into the module from the multiple module controller 56. Once programming has been downloaded into the module, however, additional commands and processes may be available. For example, the following commands may be available:

Program RAM Contents: Read and/or verify the contents of program RAM, if the module is in debug mode.

Data RAM Contents: Read and/or modify data RAM contents, if the module is in debug mode.

I/O Ports: Read input from ports or provide output from ports, if debug mode is set.

Read Voltages: Read the power supply voltages developed within the module by the power supply 358.

Status: Query present status of the module, such as reset, process running, and so on.

Software Version: Query the present software version number in RAM 32.

For each of the above commands, both prior to and after downloading of program instructions into RAM 334, the module, as described above, acknowledges the messages. Upon receipt of the message from the module controller 56, the module performs the requested process and reports the results to the multiple module controller 56, which in turn acknowledges the receipt of the message from the module.

Further, the above processes are common among the modules controlled by the multiple module controllers 54, 56. Depending on the particular function of such a module, additional function-specific commands may be issued. For example, with respect to the module 300, commands may include a command to move the system under control 374 to a new position using as pre-determined trajectory, move the system under control 374 a pre-determined amount, or read various latches within the module and as described, for example, with respect to FIG. 4.

Thus, the modular design of the automated analyzer 44 provides a consistent design approach to each of the modules, simplifying the design throughout the instrument and providing more readily reusable modules from one system to another. Because the modules are substantially electrically isolated, inter-module interference is minimized, further simplifying system design, modification and maintenance. Also, by placing local power conditioning in each of the modules, interference that might otherwise appear on a long analyzer power bus is reduced or eliminated, thereby reducing radio frequency interference (RFI).

The present invention is not to be limited to the specific embodiment disclosed herein, but is to be afforded the full scope of the appended claims and all equivalents of such claims.

I claim:

1. A modular system for use in automazed analyzers, including:
    a plurality of functionally distinct modules, each such module including serial communications means for receiving and transmitting serial communications and power supply means for receiving power and producing power for use in the module;
    bulk power supply means for supplying bulk power to the power supply means in each module;
    a serial communications loop connecting the serial communications means in the modules, the serial communications means including optical serial communication means and the serial communications loop being an optical serial communications loop for enhancing the electrical isolation between modules, and each module including communication processing means, and function specific means for handling a chemical reagent or sample for chemical analysis, and wherein the function specific means for at least one of the modules includes a motor and means for driving the motor.

2. A system as in claim 1 wherein the communications and data processing means includes an electronically alterable memory for storing a module serial number.

3. A system as claimed in claim 1 wherein the function specific means for at least one of the modules includes data acquisition means, and wherein the module including the motor is independent of the module including the data acquisition means.

4. A system as claimed in claim 1 including means for controlling the motor, the means for controlling the motor including means for limiting current applied to the motor to the maximum current, the controlling means including an integrator term integrating loop, and wherein the current limiting means includes means for reducing the integrated term loop value according to a condition that the sum of the integrator with the non-integrated term reaches a selected limit level so as to ensure that the path from the integrator to the output remains in a linear mode of operation.

5. A modular system for use in automated analyzers, including:
   a plurality of functionally distinct modules, each such module including a first portion including means for communication processing and control processing and optical serial communications means for receiving and transmitting optical serial communications, and a second portion including power supply means for receiving power and producing power for use in the module and function specific means for handling a chemical reagent or sample for chemical analysis;
   bulk power supply means for supplying bulk power to the power supply means in each module;
   a serial optical communications loop connecting the serial communications means in the modules, the optical communications loop enhancing electrical isolation between modules; and
   the function specific means for at least one of the modules including a motor and means for driving the motor.

6. A system as claimed in claim 5 wherein the function specific means for at least one of the modules includes data acquisition means, and wherein the module including the motor is independent of the module including the data acquisition means.

7. A system as claimed in claim 5 including means for controlling the motor, the means for controlling the motor including means for limiting current applied to the motor to the maximum current, the controlling means including an integrator term integrating loop, and wherein the current limiting means includes means for reducing the integrated term loop value according to a condition that the sum of the integrator with the non-integrated term reaches a selected limit level so as to ensure that the path from the integrator to the output remains in a linear mode of operation.

8. An analyzer comprising multiple modules, and at least one of the modules including a motor and motor control means and some others of the modules including data acquisition means without a motor or motor control means, and wherein each of the respective modules are independent, each module being for use in the analyzer and each module including:
   a first submodule portion including processing mens for communication and control processing and optical serial communications means for receiving and transmitting optical serial communications, the optical communications loop enhancing electrical isolation between modules;
   a second submodule portion including power supply means for receiving power and producing power for use in the module and function specific means for handling a chemical reagent or sample for chemical analysis; and
   processor means for operating in the respective module.

9. A system as claimed in claim 8 including means for controlling the motor, the means for controlling the motor including means for limiting current applied to the motor to the maximum current, the controlling means including an integrator term integrating loop, and wherein the current limiting means includes means for reducing the integrated term loop value according to a condition that the sum of the integrator with the non-integrated term reaches a selected limit level so as to ensure that the path from the integrator to the output remains in a linear mode of operation.

10. A modular system for use in automated analyzers, including:
    a plurality of functionally distinct modules, each such module including serial communications means for receiving and transmitting serial communications and power supply means for receiving power and producing power for use in the module;
    bulk power supply means for supplying bulk power to the power supply means in each module;
    a serial communications loop connecting the serial communications means in the modules, the serial communications means including optical serial communication means and the serial communications loop being an optical serial communications loop, the optical communications loop enhancing electrical isolation between modules, and each module including communication processing means, and function specific means for handling a chemical reagent or sample for chemical analysis, and wherein the function specific means for at least one of the modules includes a motor and means for driving the motor,
    the motor being a stepper motor and including motor control means for controlling the position of the stepper motor, the motor including a shaft, and the motor control means including:
    encoder means for determining the rotational position of the motor shaft;
    means for receiving a shaft target position;
    means for determining the different between the target position and the present position of the motor shaft;
    means for determining a motor current according to the different between the present position and the target position; and
    means for limiting the determined current to a maximum current, means for controlling the current applied to the motor according to the limited determined current, and wherein the current limiting means applies a current amount in excess of a maximum current value to an integrated term integrating loop in the control means, and including means for reducing an integrated term loop value and thereby stabilizing the control means.

11. A modular system for use in automated analyzers, including:
    a plurality of functionally distinct modules, each such module including serial communications means for receiving and transmitting serial communications and power supply means for converting power and producing power for use in the module;
    bulk power supply means for supplying bulk power to the power supply means in each module;
    a serial communications loop connecting the serial communications means in the modules, the serial communications means including optical serial communication means and the serial communications loop being an optical serial communications loop, the optical communications loop enhancing electrical isolation between modules, and each module including communication processing means, and function specific means for handling a chemical reagent or sample for chemical analysis, and wherein the function specific means for at least one of the modules includes a motor and means for controlling the motor, and the controlling means including means for limiting the motor current, the limiting means including an integrating control loop and the controlling means further including means for limiting the integrating control loop output according to a condition that the sum of the integrator with the non-integrated term reaches a selected limit level so as to ensure that the path from the integrator to the output remains in a linear mode of operation.

* * * * *